US009605025B2

(12) United States Patent
Dedieu et al.

(10) Patent No.: US 9,605,025 B2
(45) Date of Patent: Mar. 28, 2017

(54) ANTAGONIST PEPTIDE OF THE BOND BETWEEN CD47 AND A PROTEIN BELONGING TO THE THROMBOSPONDIN FAMILY

(75) Inventors: Stéphane Dedieu, Reims (FR); Nicolas Floquet, Saint Andre de Sangonis (FR); Laurent Martiny, Reims (FR); Christophe Schneider, Aubilly (FR); Albin Jeanne, Reims (FR); Emilie Sick, Reims (FR); Manuel Dauchez, Rosnay (FR)

(73) Assignee: Universite de Reims Champagne Ardenne, Reims (FR)

( * ) Notice: Subject to any disclaimer, the term of this patent is extended or adjusted under 35 U.S.C. 154(b) by 0 days.

(21) Appl. No.: 14/131,275

(22) PCT Filed: Jul. 6, 2012

(86) PCT No.: PCT/FR2012/051593
§ 371 (c)(1),
(2), (4) Date: Feb. 14, 2014

(87) PCT Pub. No.: WO2013/007933
PCT Pub. Date: Jan. 17, 2013

(65) Prior Publication Data
US 2014/0296477 A1    Oct. 2, 2014

(30) Foreign Application Priority Data
Jul. 8, 2011 (FR) ..................... 11 56237

(51) Int. Cl.
C07K 7/08 (2006.01)
C07K 7/06 (2006.01)
C07K 7/64 (2006.01)
C07K 14/78 (2006.01)
A61K 38/00 (2006.01)

(52) U.S. Cl.
CPC ............ *C07K 7/08* (2013.01); *C07K 7/06* (2013.01); *C07K 7/64* (2013.01); *C07K 14/78* (2013.01); *A61K 38/00* (2013.01)

(58) Field of Classification Search
CPC .......... A61K 38/00; C07K 14/78; C07K 7/06; C07K 7/08; C07K 7/64
See application file for complete search history.

(56) References Cited

U.S. PATENT DOCUMENTS 7,582,725 B2 * 9/2009 Freyberg et al. ............. 530/300
2006/0135749 A1 * 6/2006 Matozaki et al. ............. 530/350

FOREIGN PATENT DOCUMENTS

| WO | 9727873 A1 | 8/1997 | |
|---|---|---|---|
| WO | WO 2009052449 A1 * | 4/2009 | ............... C07K 7/04 |
| WO | 2010017332 A2 | 2/2010 | |

OTHER PUBLICATIONS

UniProt Protein Database, Protein Accession Q08722, Human CD47, accessed on Oct. 27, 2014.*
CNS Cancers, The Merck Manual, accessed on Oct. 27, 2014 at URL merckmanuals.com/home/brain_spinal_cord_and_nerve_disorders/tumors_of_the_nervous_system/brain_tumors.html.*
Merck Manual Breast Cancer accessed Oct. 27, 2014 at URL: merckmanuals.com/home/womens_health_issues/breast_disorders/breast_cancer.html.*
Ovarian Cancer, accessed Oct. 22, 2014 at http://www.merckmanuals.com/home/womens_health_issues/cancers_of_the_female_reproductive_system/ovarian_cancer.html.*
Merck Manual Thyroid Cancers, accessed Oct. 27, 2014, http://www.merckmanuals.com/professional/endocrine_and_metabolic_disorders/thyroid_disorders/thyroid_cancers.html.*
G.M. Rath, The C-terminal CD47/IAP-binding domain of thrombospondin-1 prevents camptothecin- and doxorubicin-induced apoptosis in human thyroid carcinoma cellsBiochimica et Biophysica Acta 1763 (2006) 1125-1134.*
Merck Manual Melanoma Cancers, accessed Oct. 27, 2014, http://www.merckmanuals.com/professional/dermatologic_disorders/cancers_of_the_skin/melanoma.html.*

* cited by examiner

*Primary Examiner* — Hasan Ahmed
*Assistant Examiner* — Erinne Dabkowski
(74) *Attorney, Agent, or Firm* — Andrew W. Chu; Craft Chu PLLC (57) ABSTRACT

Antagonist peptide of the bond between CD47 and a protein belonging to the thrombospondin family has the sequence S1 R1-R2-R3-S-Q-L-L-K-G-R4-R5-R6 and interacts specifically with the C-terminal end of the TSP, at the site of the bond between the TSP and the CD47 receptor. Interaction between the CD47 receptor and the protein is prevented. The peptide can be used in the context of cancer treatments.

2 Claims, 3 Drawing Sheets

ANTAGONIST PEPTIDE OF THE BOND BETWEEN CD47 AND A PROTEIN BELONGING TO THE THROMBOSPONDIN FAMILY

RELATED U.S. APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

BACKGROUND OF THE INVENTION

1. Field of the Invention

This invention concerns the field of molecular interactions between two proteins.

More particularly the invention concerns the interactions between an extracellular protein belonging to the thrombospondin family and a receptor, CD47, situated on the surface of the cell membrane.

This invention will have potential applications mainly in the field of tumor, thrombotic and cardiovascular diseases.

More particularly the invention relates to a peptide with the ability to bind specifically the CD47-binding domain of a protein belonging to the thrombospondin family, in such a way as to prevent the binding between the two protagonists.

2. Description of Related Art Including Information Disclosed Under 37 CFR 1.97 and 37 CFR 1.98.

Thrombospondins (TSP), and in particular TSP1 and TSP2, are proteins known to have the ability to bind to the CD47 receptor, which creates a signal inducing a cellular response on the part of the cell. Such an interaction seems to play an important role in particular in fundamental cellular processes, such as the regulation of programmed cell death, also known as apoptosis, or inflammation.

For example, work recently done by the inventors has revealed the anti-apoptotic role of TSP1 on human follicular thyroid carcinoma cells, also known as FTC cells (Rath et al., 2006). Other studies have also shown that a reduction in the expression of TSP1 leads to the reversibility of the phenotype of squamous cell carcinoma thanks to the use of an antisense strategy.

Further research carried out to try and demonstrate the role of TSP1 in the development of breast cancer cells, has, however, had contradictory outcomes; in fact, some of the research has concluded that TSP1 has a pro-apoptotic effect, that is to say that it suggests that it inhibits the growth of the mammary tumor (Esemuede et al., 2004; Manna and Frazier 2004). On the contrary, however, other studies defend the opposite concept, in which TSP1 appears to play an anti-apoptotic role and/or increase the invasive properties of these tumor cells (Wang et al., 1996a, 1996b).

Understanding the molecular mechanisms leading to the interaction between the proteins belonging to the thrombospondin family and their receptors, as well as the discovery of the ensuing cellular responses, therefore constitute an important step in devising therapeutic strategies designed to inhibit the development and proliferation of cancer cells.

Certain prior art documents already recommend using the properties of interaction between thrombospondins and their receptors, in particular CD47, in order to develop strategies either to reduce, or to increase, the rate of apoptosis of cells, whether these are cancerous or not.

Thus, it is known in the prior art, for example U.S. Pat. No. 7,582,725 B2, that an agent binding either the CD47 receptor or thrombospondin-1 can be used to inhibit the binding between said TSP1 and said CD47 receptor. Preventing this interaction is thought to significantly reduce the rate of apoptosis of certain cells such as fibroblasts or epithelial cells, involved in particular in the healing processes, in which they play an important role. Preferentially, with the aim of reducing the rate of apoptosis induced by the TSP1 protein, a peptide with an amino acid sequence with the general structural formula XXYVVM (SEQ ID NO: 4) is used.

However, in the case of this invention, the cells to be targeted and the goal to be reached are completely different. Indeed, the aim in our case is not to try to halt the apoptosis but, on the contrary, to promote the death of the cancer cells (apoptosis and/or necrosis). Thus, the peptide proposed in the aforementioned document is not suitable to solve the problem in question, namely to inhibit the invasive potential of cancer cells, in particular by promoting their entry into apoptosis.

The prior art also includes the use of monoclonal antibodies specifically directed either against the TSP protein, or against the CD47 receptor. This has the consequence of preventing the interaction between these two proteins, and therefore of inhibiting the ensuing cellular responses.

However, the main disadvantage of this technique is that the monoclonal antibodies directed against one or other of the proteins will not specifically bind at the precise site of binding between the TSP and the CD47. Thus, the blocking of the interaction between the two proteins may not be optimal and the fixing of the antibodies, whether on the TSP or on the CD47, may prevent the interaction of these proteins with their other natural ligands. As a result, other cellular processes, which are indispensable in the body and which use one or other of the aforementioned proteins, may also be inhibited or prevented. Furthermore, another major disadvantage of such a strategy resides in the fact that the anti-CD47 antibody may in certain cases act as an agonist of the receptor, that is to say it may activate the latter by means of the interaction.

Patent CA 244 6391 also uses the binding properties between the CD47 receptor and its ligand, the TSP1 protein. More particularly, it is the role of these two molecules in the immune response, and especially in the inflammatory response, which is exploited. The patent thus discloses the use of a monoclonal antibody directed against the CD47 receptor in order, in particular, to inhibit the activity of the suppressor T cells. Such inhibition is thought to play a beneficial role in various cellular processes, in particular in neutralizing infectious agents, allergic reactions, autoimmune or inflammatory diseases, etc.

However, as explained above, the use of a monoclonal antibody directed against one or other of the two proteins does not constitute a satisfactory solution.

Patent WO 2010/017332 A2 also relates to the inhibition of the interaction between the CD47 receptor and thrombospondin. In particular, this patent presents the use of very varied agents to inhibit this interaction prior to the treatment of a patent by radiotherapy, so as to facilitate the surgical removal of the tumor. Indeed, preventing the TSP1/CD47 interaction is thought to favor the protection of the cells in the immune system against the damage caused by their exposure to radiation. As a result, the immune response against tumor cells is thought to be considerably increased.

However, the agents used are not suited to specifically blocking the binding of the TSP to the CD47 receptor.

SUMMARY OF THE INVENTION

The invention offers the possibility of overcoming, at least partly, the various disadvantages of the prior art by proposing an antagonist peptide of the interaction of the CD47 with proteins belonging to the thrombospondin family, in particular TSP1 and 2. In a particularly advantageous way, the peptide fixes only onto the domain of the TSP that interacts with the CD47 receptor, thereby leaving the other domains of the TSP and the entire extracellular domain of the CD47 free so that they can bind their natural ligands. The nature of the invention, that is to say the antagonist peptide, is thought to facilitate the delivery of the active substance and to improve its bioavailability in the target cells whilst limiting the immunogenicity. Another advantage resides in the fact that the antagonist peptide is capable at once of inhibiting the binding of the CD47 with TSP1 and with TSP2.

To this effect, this invention concerns an antagonist peptide of the bond between a CD47 receptor and a protein belonging to the thrombospondin family, or TSP.

The peptide according to the invention is particular in that it has the following sequence:

(SEQ ID NO: 3)
XXXSQLLKGXXX, wherein the unknown X denotes amino acids defined by R1-R6.

In a particularly advantageous way, said peptide interacts specifically with the C-terminal end of the TSP, at the binding site between the TSP and said CD47 receptor, so as to prevent an interaction between said CD47 receptor and said protein.

In one embodiment, the radicals R1, R3 and R5 each correspond to one apolar amino acid chosen from isoleucine (I) and/or leucine (L) and/or valine (V) and/or alanine (A).

In another interesting embodiment, the radicals R2 and R4 each correspond to a negatively charged polar amino acid chosen from glutamic acid (E) and/or aspartic acid (D).

Advantageously, R6 corresponds to an uncharged polar amino acid including a hydroxyl radical chosen from serine (S) or threonine (T).

Obviously, these embodiments are not limitative of the invention. Indeed, as mentioned above, the radicals R1 and R6 may correspond to cysteine (C) so as to allow cyclization of the peptide.

In a particularly advantageous way, the sequence of the peptide according to the invention is equal to following sequence identified as:

(SEQ ID NO: 1)
IEVSQLLKGDAS

In a particularly preferred embodiment, the peptide according to this invention, whose formula is given above, is cyclized.

Even more preferentially, the cyclization of said peptide is achieved by means of a disulfide bridge between two amino acids of the cysteine type (C).

Thus, in a particularly advantageous way, the peptide according to this invention has the sequence equal to the following sequence:

(SEQ ID NO: 2)
CEVSEQLLKGDAC

In one advantageous embodiment, the peptide according to the invention is obtained by recombinant production.

Even more preferentially, said peptide is obtained by chemical synthesis.

The invention also relates to the use of the peptide in the treatment of cancer.

More particularly, the peptide can be used in particular in the treatment of follicular thyroid cancer, breast cancer or melanoma.

However, this list is not exhaustive and the peptide according to the invention could also be found to be useful for treating other types of cancer, for example pancreatic or colon cancer.

The invention also relates to a use of the peptide for preventing the interaction between thrombospondin-1 and the CD47 receptor and inhibiting the anti-apoptotic effect of this interaction on cancer cells.

The invention also concerns a use of the peptide for preventing the interaction between thrombospondin-2 and the CD47 receptor and inhibiting the anti-apoptotic effect of this interaction on cancer cells.

This invention also relates to a polypeptide including a number of amino acids of less than 50 and including a peptide with a percentage of homology of at least 60% with the sequence S2 according to the invention, preferably 80% homology and even more preferably 95% homology.

This invention further relates to an isolated nucleic acid coding for the peptide according to this invention.

In this description, the international one-letter code for amino acids is used. Thus A corresponds to alanine (Ala), C to cysteine (Cys), D to aspartic acid (Asp), E to glutamic acid (Glu), F to phenylalanine (Phe), G to glycine (Gly), H to histidine (His), I to isoleucine (Ile), K to lysine (Lys), L to leucine (Leu), M to methionine (Met), N to asparagine (Asn), P to proline (Pro), Q to glutamine (Gln), R to arginine (Arg), S to serine (Ser), T to threonine (Thr), V to valine (Val), W to tryptophan (Trp) and Y to tyrosine (Tyr).

This invention has many benefits. On the one hand, the antagonist peptide fixes only on the domain of the TSP that interacts with the CD47 receptor, thereby leaving the other domains of the TSP and the entire extracellular domain of the CD47 free so that they can bind with their natural ligands. This facilitates the delivery of the active substance, here the antagonist peptide, and improves its bioavailability in the target cells whilst limiting the immunogenicity. On the other hand, the antagonist peptide also inhibits at once the binding of the CD47 with TSP1 and with TSP2. In fact, most of the work has been done on TSP1, but the latter shows a high degree of homology with TSP2.

Moreover, this percentage of homology between TSP1 and TSP2 is particularly high at their carboxy-terminal (C-terminal) end, and even more particularly in the sequence in question, which leads us to believe on the one hand that TSP2 acts in a similar way to TSP1 as regards the CD47 receptor and on the other hand that the peptide according to this invention will also inhibit the interaction between the TSP2 protein and the CD47 receptor.

BRIEF DESCRIPTION OF THE DRAWINGS

Other features and advantages of the invention will become clear from the detailed description that follows of the non-limitative embodiments of the invention, with reference to the figures attached.

DETAILED DESCRIPTION OF THE DRAWINGS

The proteins belonging to the thrombospondin family and in particular thrombospondins-1 and -2, respectively TSP1 and TSP2, are macromolecules of the extracellular matrix. They are involved in the modulation of numerous interactions between the matrix and the cell and between the cells themselves.

More particularly, thrombospondins are glycoproteins with a multidomain structure, each domain being involved in a variety of functions as a result of its ability to bind a large number of cell surface receptors.

The thrombospondin family includes five proteins, TSP1 to TSPS, and is divided into two subgroups. TSP1 and TSP2 belong to the first of these two groups, because both have a similar structure: they are homotrimers consisting of three identical subunits. These three monomers, each with an approximate molecular mass of 150,000 Da, are connected to each other by disulfide bridges. The TSP1 and TSP2 monomers have a degree of homology which increases gradually from the N-terminal end (32% homology) towards the C-terminal end (82% homology). Furthermore, most of the adhesion sequences of TSP1 are also found in TSP2. As a result, and as pointed out above, it is highly probable that TSP2 has similar functions to TSP1.

As for TSPS 3 to 5, they are homopentamers. Their structures and their sequences are therefore different to those of TSP1 and 2.

As we have already seen, thrombospondins are proteins found in the extracellular matrix. Thus, these proteins, and in particular TSP1, influence the structure and composition of the extracellular matrix as well as the cellular phenotype due to the interactions that they can establish.

In vitro, the vascular wall cells cultured, endothelial cells, smooth muscle cells and fibroblasts, synthesize and secrete TSP1, which they also integrate in the extracellular matrix. In vivo, TSP1 is detected in the first stages of embryogenesis then during embryonic development in the regions of cell migration. In adults, it is found in particular expressed in high concentrations in injured or inflamed tissues at the beginning of the tissue repair process. TSP1 can also be synthesized and secreted by cells involved in the immune response, such as platelets, monocytes, alveolar macrophages, etc.

Thrombospondins, and in particular TSP1, are involved in various fundamental cellular processes. Thus, TSP1 influences numerous cell functions, such as platelet activation, angiogenesis, wound healing, programmed cell death and tumor progression (Sid et al., 2004). TSP2 has a domain structure similar to that of TSP1 and, as a result, some of the functions exerted by TSP2 are similar to those of TSP1. In particular, these two proteins inhibit angiogenesis (Mirochnik et al., 2008), which is a process that enables the growth of new blood vessels from pre-existing blood vessels.

More particularly, research work done by the inventors has revealed the anti-apoptotic role of TSP1 on human follicular thyroid carcinoma cells (Rath et al., 2006). In this respect, the inventors have proved that TSP1 plays an important role in tumor cells' resistance to chemotherapeutic agents, in particular doxorubicin and camptothecin. These two agents exert a cytotoxic effect by inducing apoptosis in numerous cell types.

Figure 1:
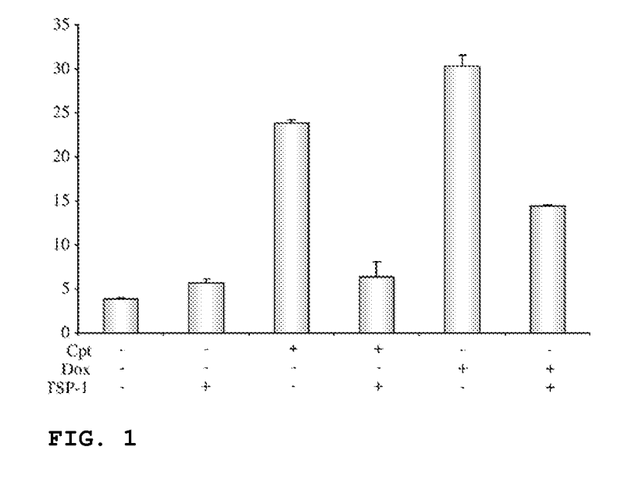
FIG. 1 is a graph illustration showing the caspase-3 activity, a marker of apoptosis, obtained by measuring the quantity of para-nitroaniline released per hour per µg of protein (y-axis). The caspase-3 activity is measured on follicular thyroid carcinoma cells in the presence of an anticancer molecule inducing apoptosis, camptothecin (Cpt) or doxorubicin (Dox) in the presence or absence of TSP1.

Referring to FIG. 1, we can see that the caspase-3 activity, considered as a good marker of cells entering apoptosis, is inhibited considerably in the presence of TSP1 compared to the same activity in the presence of doxorubicin or camptothecin, but in the absence of TSP1. The latter therefore reduces the rate of apoptosis of the thyroid carcinoma cells subjected to an anti-cancer therapy.

The authors have also shown that the level of expression of TSP1 is correlated with the invasive potential of the thyroid carcinoma cells using two cancer cell lines (FTC-138 and FTC-133) with a different invasive capacity (Sid et al., 2008).

Afterwards, the use of the peptide 4N1, with the sequence KRFYVVMWK (SEQ ID NO: 5), allowed the C-terminal end of TSP1 to be identified as responsible for the anti-apoptotic effect. In fact, this peptide is capable of establishing a molecular interaction with the CD47 receptor, which will cause a response on the part of the cell.

The CD47, also known as IAP for "integrin-associated protein", is a transmembrane receptor belonging to the immunoglobulin family, which is expressed on the great majority of cells. The extracellular domain of the CD47 plays a central role in the response of human cells and tissues after binding the C-terminal part of TSP1 or TSP2.

The inventors therefore sought to understand the role of the peptide 4N1 and the CD47 receptor in the inhibition of the apoptosis of cancer cells, and in particular the FTC-133 cells of human thyroid carcinoma (Rath et al., 2006).

Figure 2:
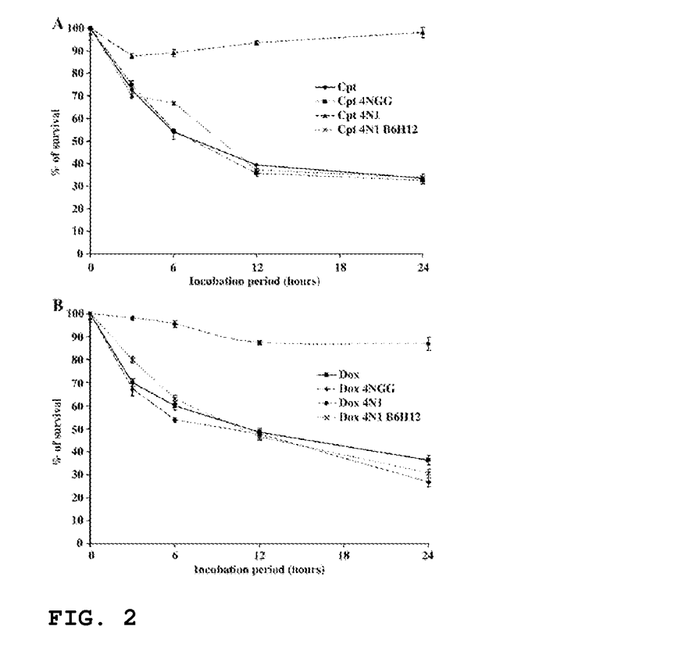
FIG. 2 is a graph illustration showing the role of the peptide 4N1 (KRFYVVMWK (SEQ ID NO: 5), derived from the C-terminal domain of TSP1, and the CD47 receptor on the regulation of apoptosis induced by camptothecin (Cpt) or doxorubicin (Dox). To achieve this, thyroid carcinoma cells (FTC-133) were incubated with 5 µM of one or other of the drugs and 100 µM of test peptide 4N1 with or without B6H12 antibody (100 µg/mL) blocking the CD47 receptor. The same experiment was performed with a control peptide 4NGG (KRFYGGMWK SEQ ID NO:6), which is incapable of binding the CD47.

As can be seen in FIG. 2, in the presence of exogenous peptide 4N1, the viability of the tumor cells is greater than that of the cells treated only with one or other of the two drugs, camptothecin and doxorubicin, or with the control peptide 4NGG.

The peptide 4N1, derived from the C-terminal end of TSP1, therefore has anti-apoptotic properties that induce a resistance of thyroid carcinoma cells to anti-cancer molecules of the camptothecin and doxorubicin type. The control peptide 4NGG, however, does not have any effect on the reduction of the number of tumor cells induced by the two aforementioned drugs.

Furthermore, in the presence of the peptide of interest 4N1 and when the B6H12 antibody blocking the CD47 is added, said peptide no longer protects the tumor cells against the anti-cancer drugs used.

The different results obtained therefore prove that thrombospondin, and in particular TSP1, interacts with the tumor cells by binding by the intermediary of its C-terminal end to a receptor, CD47. The receptor CD47 therefore represents a membrane protein that acts as a "relay" in the negative regulation of the apoptosis of tumor cells by the peptide 4N1 located at the C-terminal end of TSP1.

These results also show that numerous peptide sequences proposed in the prior art, identical or very similar to that of the peptide 4N1, are clearly not suitable for use in this case. In fact, said peptide effectively has the ability to fix onto the CD47 receptor and, as a result, causes the inhibition of the binding between the latter and a protein of the TSP1 or TSP2 type. However, the results above prove that such a bond between the peptide 4N1 and the CD47 receptor increases the viability of tumor cells and their resistance to certain drugs. The peptide 4N1 therefore acts as an agonist of the CD47 receptor.

It is then as part of an original and inventive step that the inventors sought to find out more about the molecular interactions between the CD47 receptor and TSP1 responsible for the biological effects mentioned above and in particular the anti-apoptotic effect on tumor cells.

Molecular modelling of the C-terminal end of TSP1, and more particularly modelling of the interaction between the region containing the 4N1 sequence and the CD47 receptor, was therefore undertaken.

The technique of normal mode analysis was then used in order to identify the movements of the C-terminal part of TSP1 (Floquet et al., 2008). This technique was universally favored because classical molecular dynamics simulations alone and experimental biophysical methods do not produce satisfactory results. Furthermore, the interaction between the CD47 receptor and TSP1 cannot be explained only by the crystal structure of TSP1 available in the Protein Data Bank (PDB). In fact, the TSP1 structure available, obtained by X-ray diffraction only allows the 4N1 sequence to be described as being completely buried within a hydrophobic pocket of the TSP1 protein, thereby rendering impossible any interaction of said sequence with a ligand.

Figure 3:
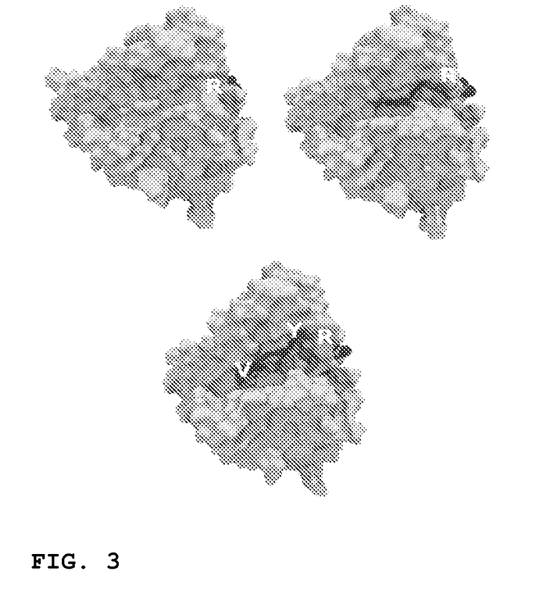
FIG. 3 is a schematic illustration representing the opening dynamics of the C-terminal domain of the TSP1 protein revealing the peptide 4N1 (KRFYVVMWK (SEQ ID NO: 5) whose amino acids are represented by darker colored spheres.

The results obtained by Floquet et al. (2008), illustrated in FIG. 3, allow the mechanism leading to the interaction between the peptide 4N1 and the CD47 receptor to be explained. In fact, the analyses showed in particular that the hydrophobic pocket, in the TSP1 protein, opens when it comes near to the CD47 receptor by means of an electrostatic "velcro" effect. This opening then reveals and renders accessible the biologically active sequence of the peptide 4N1; the interaction between TSP1, by the intermediary of the said peptide, and the CD47 receptor can then take place.

The opening movement of the hydrophobic pocket was then explored in more detail and this enabled different structures of the TSP1 protein, open to varying degrees, to be generated.

In parallel, several models of the extracellular part of the CD47 receptor were generated using the homology modelling technique.

Figure 4:
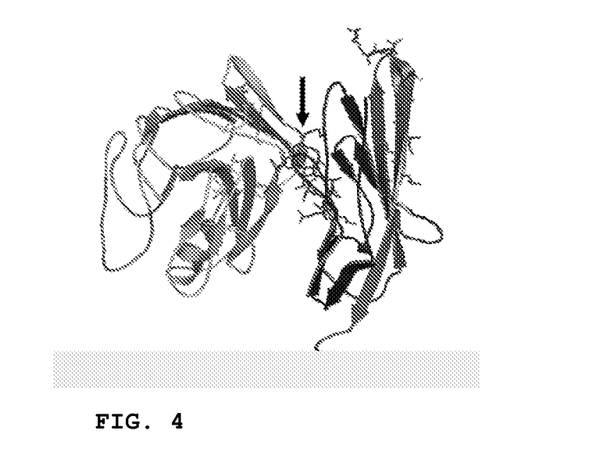
FIG. 4 shows a schematic illustration of a model of molecular interaction between the C-terminal domain of TSP1 (on the left of the figure) and the extracellular domain of the CD47 receptor (linked to the cell membrane shown in light grey). This model is obtained by the protein-protein docking technique. The arrow visible between the two proteins corresponds to the area of molecular interaction.

Further analyses, carried out using the protein-protein docking method, also made it possible to predict the potential region of interaction between the open TSP1 structure and the CD47 receptor. The results obtained can be seen in FIG. 4.

The interaction models obtained then enabled peptide fragments to be proposed mimicking the CD47 receptor sequences involved in the interaction with the TSP1 protein.

The peptides proposed are therefore advantageously able to fix on the C-terminal end of TSP1, and in particular in the region of interaction constituted by the peptide 4N1, when the latter is accessible, in particular in the case of the proximity of the CD47 membrane receptor. In other words, the peptides according to the invention enable the TSP1/CD47 interaction to be antagonized by fixing very specifically on the TSP1 at the binding site between these two proteins.

In this way, the CD47 cellular receptor remains free and can interact freely with its usual ligands, as well as TSP1. Furthermore, the other domains of the TSP1 protein also keep their binding capacity. The peptide according to this invention is therefore particularly advantageous when we know how important these two proteins TSP1 and CD47 are in numerous fundamental cellular processes.

In a particularly interesting embodiment, the peptide chosen to antagonize the bond between the TSP1 protein and the CD47 receptor corresponds to a short sequence in the extracellular domain of said receptor, and more particularly a dodecapeptide with the following sequence:

XXXSQLLKGXXX, (SEQ ID NO: 3)

wherein the unknown X denotes amino acids defined by R1-R6

Preferentially, R1 corresponds to an amino acid belonging to the apolar amino acid group, that is to say isoleucine (I) or leucine (L) or valine (V) or alanine (A). The same applies to R3 and R5

In an interesting embodiment, the R2 amino acid belongs to the group of negatively charged polar amino acids, that is to say glutamic acid (E) or aspartic acid (D). The same applies to R4

Advantageously, the R6 amino acid belongs to the group of uncharged polar amino acids with a hydroxyl radical (—OH). Thus R6 corresponds either to serine (S), or to threonine (T).

The central hexapeptide, with the formula

SQLLKG, (SEQ ID NO: 7)

is particularly advantageous for enabling the binding of the peptide according to the invention on the C-terminal domain of TSP1. The amino acids that precede or follow it in sequence S1 can be modified, but it is preferable to keep this hexapeptide for optimal binding with the TSP1 protein.

In a particularly advantageous embodiment, the dodecapeptide according to this invention has a sequence S1 that corresponds to the following sequence identified as:

IEVSQLLKGDAS (SEQ ID NO: 1)

In fact, this particular sequence S2 is optimal for antagonizing the interaction of the TSP1 protein with the CD47 receptor.

We already know, thanks to the results of the earlier research done by the inventors, that blocking TSP1/CD47 binding leads to a lifting of the inhibition of the apoptosis of the cancer cells in human thyroid carcinoma (Rath et al., 2006). As a result, the use of the peptide according to the invention enables, in particular but not limitatively, an inhibition of the invasion of the tissues by the tumor cells of thyroid carcinoma.

Work was then done to confirm these results using tumor cells from other types of cancer.

Thus, MDA-MB-231 cells corresponding to cells from a breast cancer were incubated for 24 hours with or without the dodecapeptide according to this invention. In particular, the peptide used was the one with sequence:

IEVSQLLKGDAS. (SEQ ID NO: 1)

Figure 5:
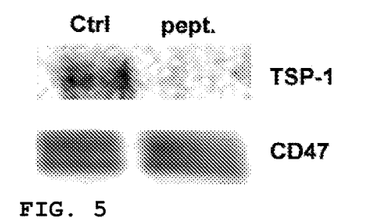
FIG. 5 is a photo illustration showing the inhibition of the biomolecular interaction between the TSP1 and the CD47 receptor of the MDA-MB-231 breast cancer cells. The cells are incubated for 2 hours with (Ctrl) or without (pept.) 100 µM of the antagonist peptide according to the invention. The TSP1/CD47 complexes are then immunoprecipitated using an anti-CD47 antibody, then the presence of TSP1 and CD47 is analyzed using the Western Blot technique.

Immunoprecipitation of the complexes, with an antibody directed against the CD47, then an analysis of the TSP1 and CD47 proteins by the Western Blot method were then done. The results are shown in FIG. 5. As can be seen, TSP1 is no longer detected by the Western Blot analysis after immunoprecipitation when the cancer cells have been incubated with the antagonist peptide according to the invention. This means that the treatment with the peptide prevents the molecular interaction between the TSP1 protein and the CD47 receptor.

The invention also relates to a polypeptide including a number of amino acids of less than 50 and including a peptide with a percentage of homology of at least 60% with the sequence S2 according to the invention, preferably 80% homology and even more preferably 95% homology.

In fact, a proportion of 7 amino acids out of a total of 12, which corresponds to a percentage of homology of 60%, constitutes a minimum active sequence sufficient to inhibit the binding between the TSP1 and the CD47 receptor.

The use of nonpeptide structural analogs of the sequence according to the invention can also be envisaged to inhibit TSP1/CD47 binding.

In a particularly interesting embodiment, the peptide according to the invention is cyclized. In fact, it has been found that the segment of CD47 corresponding to the peptide of this invention forms a loop within the receptor. Thus, such cyclization is advantageous for it enables the interaction between said peptide and the C-terminal end of the TSP1 protein to be stabilized, which has the effect of improving the biological activity and effectiveness of the peptide. Furthermore, molecular dynamics calculations on different peptides showed that it was possible to stabilize the local structure by carrying out a cyclization of said peptides.

The cyclization of the antagonist peptide according to the invention can be done by any means adapted to this purpose and known to the person skilled in the art. In particular, it is advantageous to carry out the cyclization by means of an amide bond.

Even more preferentially, the cyclization of the peptide of interest is carried out by means of a disulfide bridge, which is a strong covalent bon that couples the thiol functions (—SH) of two amino acids of the cysteine (C) type.

Choosing a disulfide bridge to obtain a cyclopeptide is particularly advantageous as it enables the peptide to be kept in zwitterionic form at a physiological pH. A molecule in zwitterionic form has an amino group with a positive charge and a carboxyl group with a negative charge. The zwitterionic form is advantageous as it enables the molecule to retain good solubility in an aqueous solution.

Thus, in a particularly preferred embodiment of the invention, the dodecapeptide has a sequence that corresponds to the sequence identified: CEVSQLLKGDAC (SEQ ID NO:2). The R1 and R6 radicals present at both ends have each been replaced by a cysteine. The two cysteine (C) amino acids at the ends of the peptide will allow the formation of a disulfide bridge (—S—S—) between their respective thiol functions.

The peptide with the sequence S3 above has the same results as the non-cyclized peptide with sequence S2 as far as the TSP1/CD47 complex immunoprecipitation experiment carried out with anti-CD47 antibodies is concerned. In conclusion, the cyclopeptide also prevents the molecular interaction between the TSP1 protein and the CD47 receptor.

The action of the cyclized dodecapeptide with sequence

CEVSQLLKGDAC (SEQ ID NO: 2)

was also tested directly in vivo on a B16-F1 mouse melanoma model injected into syngeneic C57Bl/6 mice. The results are shown in FIGS. 6 and 7.

Figure 6:
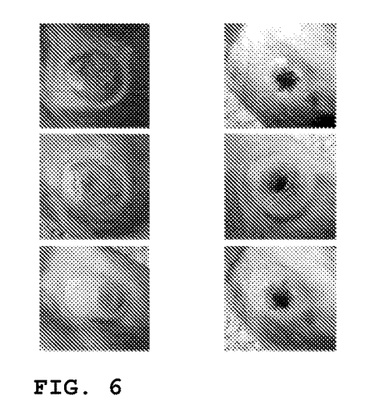
FIG. 6 is a photo illustration showing the action of the cyclized antagonist peptide on mouse melanoma cells. After a subcutaneous injection of 250,000 B16-F1 mouse melanoma cells into syngeneic C57Bl/6 mice, intraperitoneal administrations of 10 mg/kg of the antagonist were given on days 3, 5 and 7. The mice were then sacrificed and the tumors photographed on day 20.

FIG. 6 illustrates the appearance of the tumors on day 20 following the injection of the melanoma cells into the C57Bl/6 mice and after possible treatment of the animal with the cyclized peptide of interest. The half of the mice (4/8) which were treated with said peptide (on the right in the figure) showed a large necrotic area located in the tumor whereas none of the "control" mice showed any such necrosis.

Figure 7:
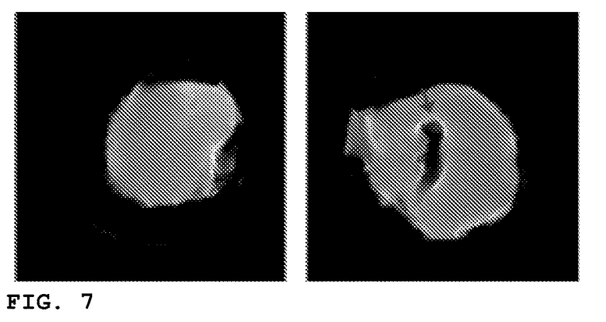
FIG. 7 is a photo illustration corresponding to an MRI analysis of an untreated tumor (on the left) and a tumor treated with the cyclized peptide of interest on day 12. An arrow points to the necrotic area.

FIG. 7 allows a comparison, thanks to a magnetic resonance imaging (RMI) analysis, of the tumor taken from the animal not treated with the tumor taken from the animal treated with the cyclized peptide by means of a disulfide bridge on day 12 after the injection of the tumor cells.

It can be seen in this figure that the tumor from the animal treated using the cyclized peptide according to the invention has a necrotic area, highlighted by an arrow. On the contrary, the same tumor from an animal not treated does not have any necrotic area. Said peptide therefore has an antitumor activity.

The peptide according to this invention, and in particular the cyclized peptide, can therefore be used in the treatment of follicular thyroid carcinoma, breast cancer or melanoma. However, such uses are not (imitative and it can easily be imagined that the peptide according to the invention could be used to treat numerous different cancers as well as those mentioned above.

Figure 8:
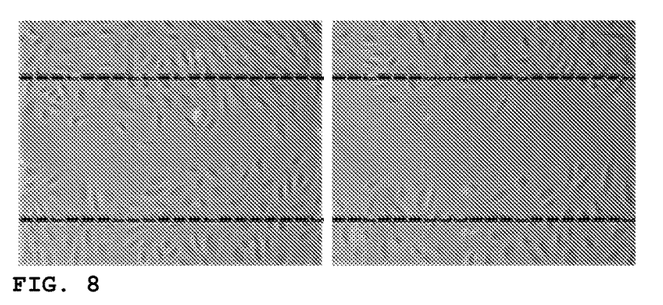
FIG. 8 is a photo illustration corresponding to a photograph of cells observed under a phase contrast microscope, enlarging 100λ. HUVEC cells (human umbilical vein endothelial cells) are first pre-treated with an antimitotic molecule, mitomycin (10 µg/mL), for 2 hours at 37° C., then a wound is made in the confluent cell layer. The cells are then incubated for 9 hours at 37° C. with the peptide described in the invention. The photograph on the left corresponds to the "control" cells whilst that on the right shows the cells treated with the peptide of interest (100 µM).

Another benefit of the invention, illustrated in FIG. 8, is that the peptide of interest inhibits tumor angiogenesis.

Angiogenesis is a normal physiological process, occurring for example during embryonic growth. However, angiogenesis can also correspond to an essential pathological process in the growth of malignant tumors and metastasis. In fact, malignant cells require oxygen and nutrients in order to grow. To obtain them, the cells will induce the formation of new blood vessels using pre-existing blood vessels in the adjacent healthy tissue. When these new vessels are formed, on the one hand they facilitate the growth of the tumor, but also the spread of the cancer cells to remote organs.

Angiogenesis is a process that takes place in three phases:

sprouting, which corresponds initially to an activation of the cells causing damage to the basement membrane and the surrounding extracellular matrix and then to a migration of endothelial cells. The cells proliferate and are differentiated into capillary-like structures to form a blood vessel.

intussusception, during which the blood vessels already formed are enlarged and separated.

septation, during which endothelial cells grow inside the vessels creating separate vascular channels.

Thrombospondins, and in particular TSP1, are known to play a role in the modulation of angiogenesis, especially in tumors.

The interaction between the CD47 receptor and TSP1 in particular is known to have an anti-angiogenic effect. The use, in the case of tumors, of the peptide according to the invention could therefore a priori turn out to be risky due to the suppression of this anti-angiogenic effect and the risk of a potential vascularization of the tumor. However, the studies carried out by the inventors have shown that, contrary to what could be expected and very surprisingly, the peptide according to the invention has an anti-angiogenic effect on the cells tested.

In fact, TSP1, as well as its interaction with the CD47 receptor, can also bind with the CD36 receptor. Such a TSP1/CD36 interaction would therefore appear to have an anti-angiogenic effect on tumor and/or endothelial cells. Thanks to the peptide according to this invention, and as we have already seen, the TSP1/CD47 interaction is prevented. However, the binding between TSP1 and the CD36 receptor can still take place, due to the extreme specificity of the peptide of interest which does not prevent TSP1 from binding with other ligands. Furthermore, given that the TSP1 no longer binds to the CD47 receptor, a larger proportion of TSP1 will be able to fix onto the CD36, which will lead to an even greater inhibition of tumor angiogenesis.

The photograph in FIG. 8 illustrates the migration of HUVEC cells, in the presence and in the absence of antagonist peptide, after these cells have been subjected to a wound whose contours are shown by a dotted line. The results are representative of 4 separate experiments and they clearly show that the first phase of the process of angiogenesis, namely the cell migration, is inhibited in the presence of the antagonist peptide according to the invention.

Thus, due to the extreme specificity of the antagonist peptide according to the invention, the TSP1 protein can still bind the CD36 receptor. However, other interactions between TSP1 and/or CD47 and membrane or even soluble proteins are also possible. In particular, interactions with membrane proteins of the integrin, HSPG (heparin sulfate proteoglycan), SIRP (signal regulatory protein) types etc. could possibly participate in and reinforce the anti-tumor effect and/or the anti-angiogenic effect of the antagonist peptide.

As far as the synthesis of the peptide of interest according to this invention is concerned, it can be done, in particular but not limitatively, by recombinant production. To this effect, a nucleic acid sequence, preferentially DNA, coding for said peptide may be introduced into a host cell, preferentially by means of a vector.

Thus this invention further relates to an isolated nucleic acid coding for the peptide according to this invention. Preferentially, this will be DNA, but it could also be RNA.

Even more preferentially, said peptide can also be acquired by a classic chemical synthesis technique known to the person skilled in the art.

The peptide according to this invention therefore has numerous and varied advantages. For example, its short sequence is easy to obtain, in particular by the classic chemical synthesis techniques.

However, the most considerable advantage lies in the fact that the peptide specifically blocks TSP1/CD47 binding. More particularly, it is the C-terminal end of the TSP1 that is blocked. Thus, the other domains of the TSP1 protein can continue to interact with their respective ligands. In particular, the TSP1 domain including the type I repetition domain (properdin homology domain) can interact with the CD36 cellular receptor, which leads to an inhibition of angiogenesis. Thus, we obtain a reduction in the vascularization of the tumor and, as a result, an inhibition of cancer cell invasion. The CD47 receptor also remains free and can then bind its natural ligands. Furthermore, there is no risk of the peptide according to the invention being an agonist of the CD47 receptor, as some molecules already used in the prior art to block the TSP1/CD47 interaction can be, such as anti-CD47 antibodies or the peptide 4N1.

Thus, the antagonist peptide has numerous potential applications in various diseases, notably tumors, and particularly for follicular thyroid carcinoma, breast cancer or melanoma, where it should limit the tumor and/or metastatic development of cancer cells. For example, said peptide is thought to enable a potentiation of the effects of chemotherapy treatments which induce apoptosis in certain types of cancer cells; in fact, the peptide of interest should contribute to reducing the resistance of cancer cells to these treatments.

Finally, given that numerous bibliographical references attribute to TSP protein a high vasoconstrictor potential and that the peptide according to the invention is liable to have an impact on the development of pro-angiogenic strategies, potential applications in the fields of cardiovascular and brain disease may therefore also be envisaged.

BIBLIOGRAPHICAL REFERENCES

N. Esemuede, T. Lee, D. Pierre-Paul, B. Sumpio, V. Gahtan, The role of thrombospondin-1 in human disease. J. Surg. Res. 122 (2004) 135-142

N. Floquet, S. Dedieu, L. Martiny, M. Dauchez, D. Perahia, Human thrombospondin's (TSP-1) C-terminal domains open to interact with the CD-47 receptor: a molecular modeling study. Arch. Biochem. Biophys. 478 (2008) 103-109

P. Manna & W. Frazier, CD47 mediates killing of breast tumor cells via Gi-dependent inhibition of protein kinase A. Cancer Res. 64(2004) 1026-36

Y. Mirochnik, A. Kwiatek, O. Volpert, Thrombospondin and apoptosis: molecular mechanisms and use for design of complementation treatments Curr. Drug Targets 2008 9(10) 851-862

G. Rath, C. Schneider, S. Dedieu, B. Rothhut, M. Soula-Rothhut, C. Ghoneim, B. Sid, H. Morjani, H. El Btaouri, L. Martiny, The C-terminal CD47/IAP-binding domain of thrombospondin-1 prevents camptothecin- and doxorubicin-induced apoptosis in human thyroid carcinoma cells. Biochim. Biophys. Acta 1763 (2006) 1125-1134

B. Sid, B. Langlois, H. Sartelet, G. Belton, S. Dedieu, L. Martiny, Thrombospondin-1 enhances human thyroid carcinoma cell invasion through urokinase activity. Int. J. Biochem. Cell. Bio. 40 (2008) 1890-1900

B. Sid, H. Sartelet, G. Belton, H. El Btaouri, G. Rath, N. Delorme, B. Haye, L. Martiny, Thrombospondin 1: a multifunctional protein implicated in the regulation of tumor growth. Crit. Rev. Oncol. Hematol. 49 (2004) 245-258

T. Wang, X. Qian, M. Granick, M. Solomon, V. Rothman, D. Berger & Tuszynski, Inhibition of breast cancer progression by an antibody through a thrombospondin-1 receptor. Surgery 120 (1996a) 449-454

T. Wang, X. Qian, M. Granick, M. Solomon, V. Rothman, D. Berger & Tuszynski, Thrombospondin-1 (TSP-1) promotes the invasive properties of human breast cancer. J. Surg. Res. 63(1996b) 39-43

We claim:

1. A complex, comprising:

an antagonist peptide and at least one thrombospondin protein, the peptide comprising: the sequence consisting of: R1-R2-R3-Ser-Gln-Leu-Leu-Lys-Gly-R4-R5-R6 (SEQ ID NO:3), wherein R1 is selected from a group consisting of: Ile, Cys, Leu, Val, and Ala, wherein R2 is selected from a group consisting of: Glu and Asp, wherein R3 is selected from a group consisting of: Ile, Leu, Val, and Ala, wherein R4 is selected from a group consisting of: Glu and Asp, wherein R5 is selected from a group consisting of: Ile, Leu, Val, and Ala, wherein R6 is selected from a group consisting of: Ser, Thr and Cys, wherein said antagonist peptide is formed by artificial synthesis; and wherein said at least one thrombospondin protein is selected from the group consisting of thrombospondin-1 and thrombospondin-2, and wherein said complex prevents an interaction between a CD47 receptor and the thrombospondin protein, the antagonistic peptide bound to a C-terminal domain of the thrombospondin protein, wherein the antagonistic peptide is a loop, said loop aligning the antagonistic peptide to the C-terminal domain on the thrombospondin protein, and wherein said loop is cyclized by an amide bond.

2. A complex, comprising:

an antagonist peptide and at least one thrombospondin protein, the peptide comprising: the sequence consisting of: R1-R2-R3-Ser-Gln-Leu-Leu-Lys-Gly-R4-R5-R6 (SEQ ID NO:3), wherein R1 is Cys, wherein R2 is selected from a group consisting of: Glu and Asp, wherein R3 is selected from a group consisting of: Ile, Leu, Val, and Ala, wherein R4 is selected from a group consisting of: Glu and Asp, wherein R5 is selected from a group consisting of: Ile, Leu, Val, and Ala, wherein R6 is Cys, wherein said antagonist peptide is formed by artificial synthesis; and wherein said at least one thrombospondin protein is selected from the group consisting of thrombospondin-1 and thrombospondin-2, and wherein said complex prevents an interaction between a CD47 receptor and the thrombospondin protein, the antagonistic peptide bound to a C-terminal domain of the thrombospondin protein, wherein the antagonistic peptide is a loop, said loop aligning the antagonistic peptide to the C-terminal domain on the thrombospondin protein, and wherein said loop is cyclized by a disulfide bridge.

* * * * *

```
                           SEQUENCE LISTING

<160> NUMBER OF SEQ ID NOS: 7

<210> SEQ ID NO 1
        <211> LENGTH: 12
        <212> TYPE: PRT
        <213> ORGANISM: Artificial sequence
        <220> FEATURE:
        <223> OTHER INFORMATION: Antagonist peptide of the bond between a
              receptor CD47 and a protein belonging to the thrombospondin family

<400> SEQUENCE: 1

Ile Glu Val Ser Gln Leu Leu Lys Gly Asp Ala Ser
        1               5                   10

<210> SEQ ID NO 2
        <211> LENGTH: 12
        <212> TYPE: PRT
        <213> ORGANISM: Artificial sequence
        <220> FEATURE:
        <223> OTHER INFORMATION: Antagonist peptide of the bond between a
              receptor CD47 and a protein belonging to the thrombospondin family

<400> SEQUENCE: 2

Cys Glu Val Ser Gln Leu Leu Lys Gly Asp Ala Cys
        1               5                   10

<210> SEQ ID NO 3
        <211> LENGTH: 12
        <212> TYPE: PRT
        <213> ORGANISM: Artificial sequence
        <220> FEATURE:
        <223> OTHER INFORMATION: Antagonist peptide of the bond between a
              receptor CD47 and a protein belonging to the thrombospondin family
        <221> NAME/KEY: misc_feature
        <222> LOCATION: (1)..(1)
        <223> OTHER INFORMATION: Xaa indicates Ile, Cys, Leu, Val or Ala
        <221> NAME/KEY: misc_feature
        <222> LOCATION: (2)..(2)
        <223> OTHER INFORMATION: Xaa indicates Glu or Asp
        <221> NAME/KEY: misc_feature
        <222> LOCATION: (3)..(3)
        <223> OTHER INFORMATION: Xaa indicates Ile, Leu, Val, or Ala
        <221> NAME/KEY: misc_feature
        <222> LOCATION: (10)..(10)
        <223> OTHER INFORMATION: Xaa indicates Glu or Asp
        <221> NAME/KEY: misc_feature
        <222> LOCATION: (11)..(11)
        <223> OTHER INFORMATION: Xaa indicates Ile, Leu, Val, or Ala
        <221> NAME/KEY: misc_feature
        <222> LOCATION: (12)..(12)
        <223> OTHER INFORMATION: Xaa indicates Ser, Thr, or Cys
```

```
<400> SEQUENCE: 3

Xaa Xaa Xaa Ser Gln Leu Leu Lys Gly Xaa Xaa Xaa
 1               5                  10

<210> SEQ ID NO 4
<211> LENGTH: 6
<212> TYPE: PRT
<213> ORGANISM: Artificial sequence
<220> FEATURE:
<223> OTHER INFORMATION: synthetic peptide
<221> NAME/KEY: misc_feature
<222> LOCATION: (1)..(1)
<223> OTHER INFORMATION: Xaa indicates any amino acid
<221> NAME/KEY: misc_feature
<222> LOCATION: (2)..(2)
<223> OTHER INFORMATION: Xaa indicates any amino acid

<400> SEQUENCE: 4

Xaa Xaa Tyr Val Val Met
 1               5

<210> SEQ ID NO 5
<211> LENGTH: 9
<212> TYPE: PRT
<213> ORGANISM: Artificial sequence
<220> FEATURE:
<223> OTHER INFORMATION: synthetic peptide

<400> SEQUENCE: 5

Lys Arg Phe Tyr Val Val Met Trp Lys
 1               5

<210> SEQ ID NO 6
<211> LENGTH: 9
<212> TYPE: PRT
<213> ORGANISM: Artificial sequence
<220> FEATURE:
<223> OTHER INFORMATION: synthetic peptide

<400> SEQUENCE: 6

Lys Arg Phe Tyr Gly Gly Met Trp Lys
 1               5

<210> SEQ ID NO 7
<211> LENGTH: 6
<212> TYPE: PRT
<213> ORGANISM: Artificial sequence
<220> FEATURE:
<223> OTHER INFORMATION: Antagonist peptide of the bond between a
      receptor CD47 and a protein belonging to the thrombospondin family

<400> SEQUENCE: 7

Ser Gln Leu Leu Lys Gly
 1               5
```